United States Patent [19]

König

[11] 4,228,038
[45] Oct. 14, 1980

[54] METHOD FOR THE PREPARATION OF CATALYST OF VANADIUM PENTOXIDE ON SUBSTRATE OF TITANIUM DIOXIDE

[75] Inventor: Peter König, Budapest, Hungary

[73] Assignee: Tioxide Group Limited, Billingham, England

[21] Appl. No.: 75,410

[22] Filed: Sep. 14, 1979

[30] Foreign Application Priority Data

Jul. 24, 1979 [GB] United Kingdom ............... 25801/79

[51] Int. Cl.³ .......................... B01J 21/06; B01J 23/22
[52] U.S. Cl. ................................. 252/461; 260/346.7
[58] Field of Search ...................... 252/461; 260/346.7

[56] References Cited

U.S. PATENT DOCUMENTS 3,215,644  11/1965  Kakinoki et al. ............... 252/476 X
4,012,338  3/1977  Urwin ............................. 423/610 X

FOREIGN PATENT DOCUMENTS 1238379  7/1971  United Kingdom .
1444799  8/1976  United Kingdom .

Primary Examiner—W. J. Shine
Attorney, Agent, or Firm—Schuyler, Birch, McKie & Beckett

[57] ABSTRACT

A method for the manufacture of a selective oxidation catalyst by heating titanium dioxide in the presence of water prior to treating the titanium dioxide with vanadium oxytrichloride in vapor form and then heating the treated titanium dioxide. This treatment with water and vanadium oxytrichloride is repeated a number of times until the desired selective oxidation catalyst is obtained.

10 Claims, No Drawings

METHOD FOR THE PREPARATION OF CATALYST OF VANADIUM PENTOXIDE ON SUBSTRATE OF TITANIUM DIOXIDE

This invention relates to an improved method for the manufacture of catalysts and particularly to the manufacture of a selective oxidation catalyst.

According to the present invention, the method for the manufacture of a selective oxidation catalyst comprises the following process stages:

(1) heating a particulate catalyst substrate comprising titanium dioxide in an atmosphere containing water vapour (2) treating the substrate with vanadium oxytrichloride in vapour form (3) heating the treated substrate until the evolution of hydrogen chloride has ceased and to complete the conversion of the deposited vanadium compound to vanadium pentoxide (4) repeating the process stages 1, 2 and 3 at least a further three times, and (5) finally allowing the treated substrate comprising the selective oxidation catalyst to cool.

The method of the present invention produces a selective oxidation catalyst suitable for use in the oxidation of aromatic hydrocarbons and particularly for the oxidation of o-xylene to phthalic anhydride.

The catalysts produced according to the method of the invention have been found to produce a very high yield of phthalic anhydride when used for the oxidation of o-xylene. The catalysts have been found to be particularly useful in this respect when the process stages 1, 2 and 3 are carried out for a total of five or six times.

The method of the invention provides a catalyst based on titanium dioxide. The titanium dioxide to be treated in the method of the invention can be that produced by the well known "sulphate" process in which titanyl sulphate is hydrolysed to form hydrous titanium dioxide and this product is then calcined at an elevated temperature. Alternatively, the titanium dioxide can be that produced by the well known "chloride" process in which titanium tetrachloride is oxidised in the vapour phase to produce the titanium dioxide particulate product without further calcination. Also the titanium dioxide to be used as the catalyst substrate can be formed by neutralising with ammonia an aqueous solution of titanium tetrachloride and the precipitated product then calcined at an elevated temperature.

If desired, the catalyst substrate can be rutile titanium dioxide or anatase titanium dioxide and, if desired, the particulate titanium dioxide can be sieved prior to treatment by the method of the invention to select an appropriate particle sized product. It has been found advantageous to employ as the catalyst substrate titanium dioxide having a particle size within the range 50 to 600 microns and surface area within the range 1 to 100 square metres per gram. The most preferred catalyst prepared by the method of the invention is one based on anatase titanium dioxide.

In the method of the present invention the catalyst substrate is heated in an atmosphere containing water vapour prior to treatment with vanadium oxytrichloride, to a temperature of 30° C. to 90° C. If necessary any excess water can be removed from the substrate by heating in a stream of say dry air. It is believed that the amount of water associated with the substrate should be such as to provide at least mono layer coverage of the surface of the substrate with water.

The catalyst substrate is then contacted with vanadium oxychloride vapour to effect adsorption of the vapour on the particles of titanium dioxide and this may be effected in any convenient form of apparatus and preferably during treatment with the vapour the titanium dioxide substrate is agitated such as in a fluidised state.

After the treatment with the vapour of the vanadium oxytrichloride the treated substrate is then heated and during this operation hydrogen chloride is evolved from the treated substrate and to complete the conversion of deposited vanadium compound to vanadium pentoxide. Preferably the substrate is heated in an oxygen-containing atmosphere, eg air. Usually the treated substrate is heated during process stage 3 to a temperature of from 70° C. to 450° C. and preferably to a temperature of the order of 400° C.

In order to produce a selective oxidation catalyst having a high selectivity it has been found necessary to repeat these process stages 1, 2 and 3 at least a further three times and as indicated previously preferably a further four or five times. During each adsorption and heating cycle more vanadium pentoxide is deposited on the surface of the titanium dioxide substrate.

Naturally the amount of vanadium compound deposited during the process stage 2 and subsequent heating stage 3 depends on the amount of vanadium oxytrichloride vapour brought into contact with the catalyst substrate and the amount absorbed. Preferably the total amount of vanadium pentoxide deposited in the method of the invention is from 0.5% to 15% by weight $V_2O_5$ on the weight of titanium dioxide and it is desirable that the amount deposited should be at least equivalent to mono-layer coverage.

The invention also includes a method for the oxidation of o-xylene to phthalic anhydride in which a catalyst prepared by the method of invention is contacted with o-xylene and the phthalic anhydride product is collected. In such an oxidation process the catalyst is placed in an oxidation column and heated to a temperature of say between 250° C. and 500° C. and through the packed bed of catalyst of mixture of air and o-xylene is passed. The use of a catalyst prepared in accordance with the method of the invention premits a selectivity of the order of 100 to be obtained in such an oxidation process.

The invention is illustrated in the following Example.

EXAMPLE

An anatase titanium dioxide prepared by the "sulphate" process and which had been previously calcined at 950° C. was selected for use as the catalyst substrate. This anatase titanium dioxide had a surface area of 10 square meters per gram and was sieved and the particle size range of 200 to 300 microns was selected for use as the substrate.

The catalyst substrate was then placed in a "U" shaped tube and a 200 torr water vapour/1 atmosphere air mixture was passed through the tube for two hours at 50° C. with a velocity of 20 ccs per minute (process stage 1). Dry air at 140° C. was then passed through the tube for a further four hours to remove excess water from the catalyst substrate. The tube was then allowed to cool to room temperature and dry air containing vanadium oxytrichloride vapour was passed through the tube overnight (process stage 2). At the completion of this time the temperature of the tube was then raised slowly to 400° C. during which time dry air was passed through the tube to remove hydrogen chloride gas and to complete the conversion of the vanadium oxytrichloride to vanadium pentoxide (process stage 3).

Six catalysts were prepared in separate experiments by carrying out stages 1, 2 and 3 for a total of 1, 2, 3, 4, 5 and 6 times respectively.

For the catalyst prepared by the method in which the substrate was treated with vanadium oxytrichloride for a total of six times, the amount of vanadium pentoxide associated with the titanium dioxide was found to be 1.7% by weight $V_2O_5$ on the weight of $TiO_2$.

Each catalyst was then used to effect the oxidation of o-xylene to phthalic anhydride. The catalyst was placed in a tube and heated at temperatures between 250° C. and 450° C. Through the packed bed so obtained within the tube there was passed a mixture of air and o-xylene and the products after passing through the bed collected. The product was found to contain phthalic anhydride. The selectivity of each catalyst was measured.

The selectivity is expressed as the weight in grams of phthalic anhydride recovered from the oxidation of 100 grams of o-xylene. As indicated the oxidation process was carried out at a range of temperatures and the temperature at which the maximum yield of phthalic anhydride is obtained is shown below together with the respective yield or selectivity in Table I. t,0070

It will be seen from the above results that the use of a catalyst manufactured in accordance with the present invention is extremely advantageous in the oxidation of o-xylene to phthalic anhydride.

What is claimed is:

1. A method for the manufacture of a selective oxidation catalyst which comprises the following process stages:

(1) heating a particulate catalyst substrate comprising titanium dioxide in an atmosphere containing water vapour
   (2) treating the substrate with vanadium oxytrichloride in vapour form
   (3) heating the treated substrate until the evolution of hydrogen chloride has ceased and to complete the conversion of the deposited vanadium compound to vanadium pentoxide
   (4) repeating the process stages 1, 2, and 3 at least a further three times, and
   (5) finally allowing the treated substrate comprising the selective oxidation catalyst to cool.

2. A method according to claim 1 in which the process stage 4 is repeated a further four times.

3. A method according to claim 1 in which the process stage 4 is repeated a further five times.

4. A method according to claim 1 in which the catalyst substrate is heated in process stage 1 to a temperature within the range 30° C. to 90° C.

5. A method according to claim 1 in which after the process stage 1 excess water is removed from the substrate by heating in a stream of dry air.

6. A method according to claim 1 in which during process stage 3 the treated substrate is heated in an oxygen containing atmosphere.

7. A method according to claim 1 in which during process stage 3 the treated substrate is heated at a temperature within the range 70° C. to 450° C.

8. A method according to claim 1 in which the catalyst after process stage 4 contains vanadium pentoxide in an amount of from 0.5% to 15% by weight $V_2O_5$ based on the weight of titanium dioxide.

9. A method according to claim 1 in which the particulate catalyst substrate has a particle size within the range 50 to 600 microns.

10. A method according to claim 1 in which the particulate catalyst substrate has a surface area within the range 1 to 100 square meters per gram.

* * * * *

UNITED STATES PATENT AND TRADEMARK OFFICE
CERTIFICATE OF CORRECTION

PATENT NO. : 4,228,038

DATED : October 14, 1980

INVENTOR(S) : Peter Konig

It is certified that error appears in the above-identified patent and that said Letters Patent is hereby corrected as shown below:

At Column 3, line 32, please insert the following Table:

TABLE I

| Number of treatments with $VOCl_3$ | Selectivity (Maximum yield of phthalic anhydride grams) | Temperature to give maximum yield (°C) |
|---|---|---|
| 0 | 0 | 385 |
| 1 | 1 | 367 |
| 2 | 25 | 401 |
| 3 | 57 | 364 |
| 4 | 86 | 354 |
| 5 | 103 | 344 |
| 6 | 103 | 343 |

Signed and Sealed this

Twentieth Day of May 1986

[SEAL]

Attest:

DONALD J. QUIGG

Attesting Officer

Commissioner of Patents and Trademarks